(12) United States Patent
Wester et al.

(10) Patent No.: US 7,771,771 B2
(45) Date of Patent: Aug. 10, 2010

(54) PHYTOSTEROL COMPOSITIONS

(75) Inventors: Ingmar Wester, Raisio (FI); Jari Ekblom, Raisio (FI)

(73) Assignee: Raisio Nutrition Ltd., Raisio (FI)

( * ) Notice: Subject to any disclaimer, the term of this patent is extended or adjusted under 35 U.S.C. 154(b) by 484 days.

(21) Appl. No.: 10/956,128

(22) Filed: Oct. 4, 2004

(65) Prior Publication Data

US 2005/0079258 A1    Apr. 14, 2005

Related U.S. Application Data

(62) Division of application No. 10/439,010, filed on May 16, 2003, now Pat. No. 6,800,317, which is a division of application No. 09/674,730, filed as application No. PCT/FI99/00379 on May 6, 1999, now Pat. No. 6,589,588.

(30) Foreign Application Priority Data

May 6, 1998    (FI) .................................... 981011

(51) Int. Cl.
  *A23D 9/00*        (2006.01)
(52) U.S. Cl. ..................... 426/611; 426/417; 426/601
(58) Field of Classification Search .................. 426/611
  See application file for complete search history.

(56) References Cited

U.S. PATENT DOCUMENTS

| | | | | |
|---|---|---|---|---|
| 3,559,153 | A * | 1/1971 | Hackmann | 439/552 |
| 3,751,569 | A | 8/1973 | Erickson et al. | |
| 4,377,526 | A | 3/1983 | Fujita et al. | |
| 4,588,717 | A | 5/1986 | Mitchell | |
| 5,502,045 | A | 3/1996 | Miettinen et al. | 514/182 |
| 6,106,886 | A * | 8/2000 | van Amerongen et al. | 426/611 |
| 6,162,483 | A * | 12/2000 | Wester | 426/607 |
| 6,231,915 | B1 * | 5/2001 | van Amerongen et al. | 426/611 |
| 6,589,588 | B1 * | 7/2003 | Wester et al. | 426/607 |
| 6,677,469 | B1 * | 1/2004 | Dunford et al. | 554/205 |
| 6,800,317 | B2 * | 10/2004 | Wester et al. | 426/417 |

FOREIGN PATENT DOCUMENTS

| | | |
|---|---|---|
| EP | 0 195 311 | 1/1996 |
| EP | 0897970 | 2/1999 |
| EP | 0911 385 A1 | 4/1999 |
| GB | 1405346 | 9/1975 |
| JP | 046668/65 | 2/1969 |
| JP | 2006404 A | 1/1990 |
| WO | 92/19640 | 11/1992 |
| WO | WO/92/19640 | 11/1992 |
| WO | 98/01126 | 1/1998 |
| WO | 98/19556 | 5/1998 |

OTHER PUBLICATIONS

Hui, Y. H. 1996. Bailey's Industrial Oil and Fat Products, 5th edition, vol. 2. John Wiley & Sons, Inc., New York, p. 613 & 615.*

Milkova et al., "Sterol composition of Bulgarian soya and corn oils", STN International, File FSTA, FSTA accession No. 77 (07): No. 375 (1977).

Mattson et al., "Effect of Plant Sterol Esters on the Absorption of Dietary Cholesterol", The Proctor & Gamble Company, pp. 1139-1146 (Sep. 9, 1974).

Ikeda et al., "Antihypercholesterolemic Activity of &-Sitostanol in Rabbits," J. Nutr. Sci. Vitaminol, 27, 243-251 (1981).

Schuhmann et al., Method of Qualitative and Quantitative Determination of Phytosterols in Vegetable Iols by LC-GC off-line, Mitt. Gebiete Lebensm Hyg. vol. 87, p. 708-715 (1996).

Dutta, "Sitostanol Fatty Acid Ester Content of Hydrogenated Rapeseed Oil" (hydrogenation results).

Swern, Bailey's Industrial Oil and Fat Products, vol. 1, 4th ed., p. 315, 370, 378, 379, 383, 394, 416, 417, 430, John Wiley & Sons, NY, NY (1979).

Denke, "Lack of Efficacy of Low-Dose Sitostanol Therapy as an Adjunct to Cholesterol-Lowering Diet in Men with Moderate Hypercholesterolemia[1-3]", Am J. Clm. Nutr., 61, pp. 392-396 (1995).

Miettinen et al., "Reduction of Serum Cholesterol with Sistostanol-Ester Margarine in a Mildly Hypercholesterolemic Population", The New England J of Med 333, 1308-1312 (1995).

Mattson, et al., "Optimizing the Effect of Plant Serous on Cholesterol Absorption in Man[1-3]", The Am J of Cl Nutr, 35, pp. 697-700 (Apr. 1982).

Dutta et al., "Saturated Sterols (Stanols) in Unhydrogenated Edible Vegetable Oils and in Cereal Lipids", J Sci Food Agric, vol. 71, p. 383-391 (1996).

Becker et al., "Treatment of Severe Familial Hypercholesterolemia in Childhood with Sitosterol and Sitostanol", J of Ped, vol. 122, No. 2, pp. 292-296 (1993).

Sugano et al., "A Comparison of Hypercholesterolemic Activity of &-Sitosterol and &-Sitostanol in Rats", Lab of Nut Chem, pp. 2011-2019 (1977).

Statement of Ikka Etupaltta, Jan. 18, 2001.

Miettinen et al., "Serum Plant Sterols and Cholesterol Precursors Reflect Cholesterol Absorption and Synthesis in Volunteers of a Randomly Selected Male Population", Am J Epid, vol. 131, No. 1, p. 20-31 (1990).

Parodi, "Fate of Dietary Sterols in Hydrogenated Oils and Fats", J of Am Oil Chem Soc, vol. 52, pp. 345-348 (1975).

Ullmann's Encyclopedia of Industrial Chemistry, vol. A16, p. 152-153 (1990).

Hiiros et al., "Elintarvike-Tekniikan Perusteet", VAPK-kustannus, Helsinki p. 236-241 (incl trans p. 240-241 (1990).

Raisio Benecol Ltd, "Formation of Sitostanol During Partial and Full Hydrogenation of Vegetable Soybean Oil with Ni-Catalyst". (Hydrogenation results).

Hallikanen et al., "Comparison of the Effects of Plant Sterol Ester and Plant Stanol Ester-enriched Margarines in Lowering Serum Cholesterol Concentrations in Hypercholesterolaemic Subjects on a Low-Fat Diet", Eur J of Cl Nut, vol. 54, p. 715-725 (2000).

(Continued)

*Primary Examiner*—Carolyn A Paden
(74) *Attorney, Agent, or Firm*—Arent Fox LLP

(57) ABSTRACT

This invention relates to phytosterols and phytostanols, in particular to fatty acid esters of phytosterols and phytostanols with a specified fatty acid composition. The invention further relates to methods for preparation of the phytosterol and phytostanol esters and their uses.

6 Claims, 4 Drawing Sheets

OTHER PUBLICATIONS

Plat et al., "Effects of Low-Fat Yogurt with Plant Stanol Esters and of Consumption Frequency on LDL-Cholesterol Levels", Summary of Pres at 92nd AOCS Annual Meeting and Expo, May 13-16, 2001, Minneapolis, Minn., USA.

PCT Applicant's Guide (Swedish Patent Office as ISA)—Annex D and E (Jul. 1999 and 1998, respectively).

Opponent's Further Submissions of Jun. 27, 2000 (Including Annexes I-III).

Sugano et al., "Stanol Compositions in Edible Fats and Oils", Sci Bull. Fac Agr, Kyushu Univ, vol. 32, No. 1, p. 21-28 (1977).

Patent Abstracts of Japan 20-6404A, Jan. 10, 1990.

A. Kuskis et al. "Preparation and Certain Physical Properties of Some Plant Steryl Esters" Journal of Organic Chemistry, 1960, 25: 1209-1219.

L. Dyas et al. "Steryl Esters in a Cell Suspension Culture of Celery (*Apium graveolens*)" Lipids, 1991; 26 (7): 536-541.

F.D. Gunstone et al., "Rapeseed oil" The Lipid Handbook, Second Edition, 1994, pp. 88-94, 97-100, 118-125.

M. Sugano et al. "Stanol Components in Edible Fats and Oils" Sci. Bull. Fac. Agr., Kyushu Univ., 1977, 32(1): pp. 21-28.

International Norm Institute, Norm NEN 3428.

J.L. Iverson et al. "Detection of Trace Fatty Acids in Fats and Oils by Urea Fractionation and Gas-Liquid Chromatography" The Journal of the American Oil Chemists' Society, 1965, 42: 1063-1067.

J.H. van Stuyvenberg, "Margarine: An Economic, Social and Scientific History 1869-1969" 1969, pp. 92-103, 202-205.

US 5,670,348, 09/1997, Cain et al. (withdrawn)

\* cited by examiner

DSC melting curve for stanol ester with fatty acids derived from soybean oil

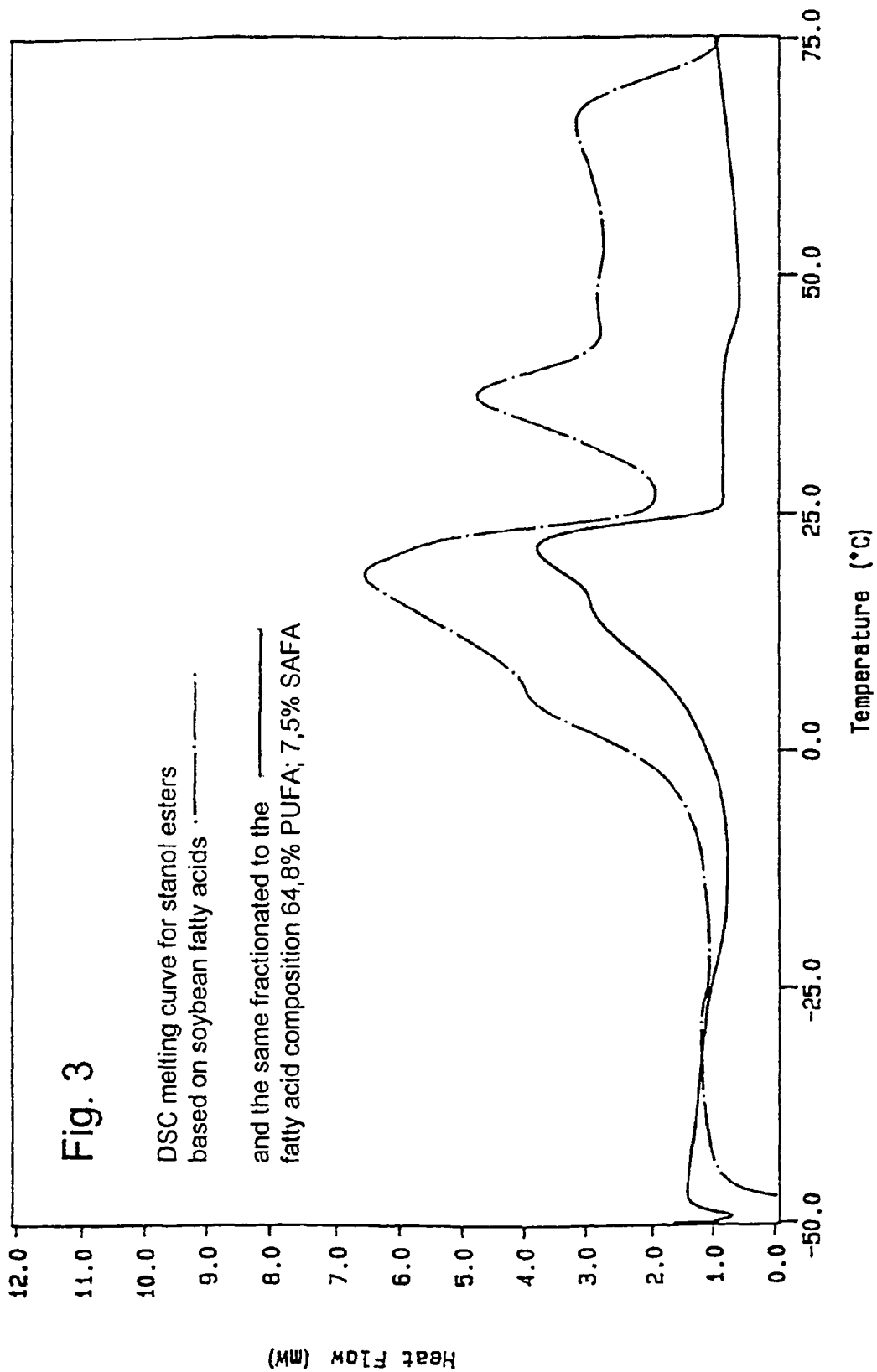

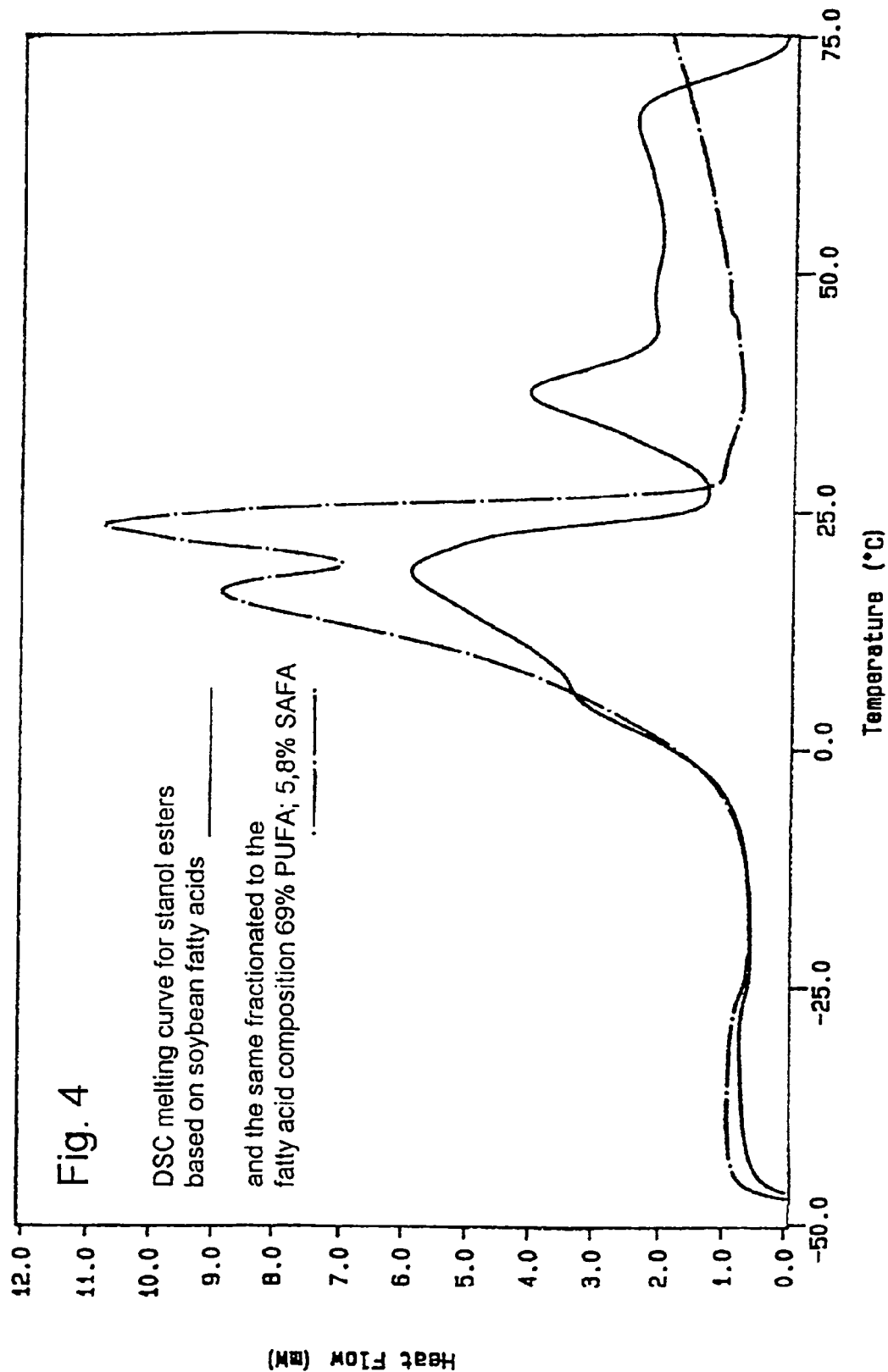

PHYTOSTEROL COMPOSITIONS

This is a divisional of U.S. patent application Ser. No. 10/439,010 filed May 16, 2003, now U.S. Pat. No. 6,800,317, which is a divisional of U.S. patent application Ser. No. 09/674,730 filed Dec. 20, 2000, now U.S. Pat. No. 6,589,588, which is a National Stage of Application No. PCT/FI99/00379 filed May 6, 1999. The disclosures of the prior applications are hereby incorporated by reference herein in their entirety.

BACKGROUND OF THE INVENTION

This invention relates to phytosterols and phytostanols, in particular to fatty acid esters of phytosterols and/or phytostanols with a specified fatty acid composition. The invention further relates to methods for preparation of the phytosterol and/or phytostanol esters and their uses.

Since the 1950's numerous studies in animals and humans have been reported, in which plant sterols (phytosterols) have caused significant reductions in serum cholesterol levels. Plant sterols reduce serum cholesterol levels by reducing the absorption of cholesterol from the digestive tract. The mechanism or mechanisms by which this reduction in cholesterol absorption is taking place is not fully known.

Phytosterols are a group of compounds structurally very similar to cholesterol. The phytosterols occurring most frequently in the nature are sitosterol, campesterol and stigmasterol. In all phytosterol preparations is sitosterol the main component. Most clinical and non-clinical studies have been conducted with so-called tall oil sterols, containing high amounts of sitosterol and some sitostanol. In the scientific literature such sterol blends are often referred to as sitosterol. Vegetable oils and fats are the main source of plant sterols in our diet. In vegetable oils a major part of the sterols exists as fatty acid esters.

In earlier study's plant sterols have been used in poorly soluble, crystalline form with high daily intakes (up to 20-30 g/day). However, even when administered in relatively small doses (a few grams per day) and under optimum conditions, plant sterols reduce serum total and LDL-cholesterol levels.

In recent years plant sterol treatment of hypercholesterolemia has been refined by the use of the fully saturated form of sitosterol, sitostanol. Saturated phytosterols such as sitostanol and campestanol are present in our diet in small amounts. Daily intake of total stanols in the Finnish diet has been estimated to 30-80 mg/day. However, tall oil sterols (sterols from pine trees) contain 10-20% of plant stanols (sitostanol+campestanol). Phytostanols can also be produced by hydrogenation to remove the doubie bond in corresponding plant sterols.

Sitostanol is virtually unabsorbed and lowers the cholesterol content of mixed micelles more efficiently than sitosterol, thus showing an enhanced serum cholesterol lowering effect Sugano et al. (Sugano M,. Morioka H. and Ikeda I. (1977) *J. Nutr.* 107, 2011-019) showed that sitostanol had a higher hypocholes-terolemic activity than sitosterol in rats. Similar results were obtained with rabbits (Ikeda I,. Kawasaki A,. Samazima K. and Sugano M. (1981). *J. Nutr. Sci. Vitaminol.* 27, 243-251). In addition, sitostanol depressed the formation of aortic atheroma due to cholesterol feeding more than did sitosterol. Becker et al. (Becker M,. Staab D. and von Bergmann K. (1993) *Journal of Pediatrics,* 122, 292-296.) showed, that sitostanol was significantly more effective than sitosterol in reducing elevated levels of LDL cholesterol in children with severe familial hypercholesterolemia.

The solubility of free sterol and especially of free stanol in edible oils and fats is very low. E.g. less than 2% free sterols are dissolvable in oils and fats if water is present. This problem can be overcomed by esterifying the free sterols with fatty acid esters. Esters of plant sterols have been shown to be equal to corresponding free sterols in reducing cholesterol absorption in rat (Mattson F. H., Volpenheim R. H. and Erickson B. A., (1977), *J. Nutr.* 107,1139-46), while Mattson et al. (Mattson F. H., Grundy S. M. and Crouse J. R., (1982), *Am. J. Clin. Nutr.* 35, 697-700) found that free sterols were more effective in reducing cholesterol absorption in man.

During fat digestion dietary fat, sterol and/or stanol ester together with dietary cholesterol and its esters reach the intestinal oil phase (in intestinal emulsion), from which free stanols and sterols are released through lipolysis by enzymes like cholesterol esterase. The released free stanols and/or sterols compete with both dietary and biliary cholesterol for micellar solubility and lower the micellar phase concentration of cholesterol when present in lipid core fat material of the mixed micelles in high enough concentrations. Plant stanols like sitostanol is more effective in lowering micellar phase cholesterol than the corresponding si-tosterol.

U.S. Pat. No. 3,751,569 (Erickson B. A.) describes clear cooking and salad oils having hypocholesterolemic properties. Into the liquid glyceride base oil is mixed 0.5-10 weight-% (as free sterol equivalent) of a sterol fatty acid ester. The cooking or salad oil was prepared by dissolving liquid glyceride base oil and plant sterols monocarboxylic acid in a mutual solvent and evaporating the solvent (hexane or diethyl ether). The fatty acid moiety was defined as a saturated monocarboxylic acid $C_{1-12}$ or an unsaturated fatty acid with up to 24 carbon atoms. The sterol ester is added in an amount small enough to prevent precipitation at refrigerating temperatures. The solubility of different fatty acid esters of phytosterol in triolein are also presented, showing very low solubility for $C_{14}$ and $C_{16}$ saturated fatty acid phytosterol esters. This patent discloses the use of certain individual fatty acid esters of phytosterols added to the cooking or salad oil in relatively small amounts.

Saturated plant sterols have been shown to be more effective in reducing the absorption of cholesterol from the digestive tract and thus causing enhanced reduction of total and LDL serum cholesterol levels. Saturation of plant sterols to plant stanols further decreases their solubility in oils and fats. U.S. Pat. No. 5,502,045 (Miettinen et al.) discloses a method for producing fatty acid esters of sitostanol and the use of the substance for lowering high cholesterol levels. By esterifying the sitostanol blend with fatty acids from a vegetable oil such as rapeseed oil (LEAR) a fat-soluble stanol ester was obtained. Examples are given showing that up to 20% of the normally used fat blend can be exchange with this sitostanol fatty acid ester blend based on low erucic acid rapeseed oil fatty acid esters. The incorporation of such fat-soluble stanol ester to food products like margarines and spreads provides a way to introduce the adequate daily amount of stanol for optimal reduction of the cholesterol absorption.

In several clinical studies these fat-soluble stanol esters have proven to be very effective in reducing the absorption of cholesterol from the digestive tract. The North Karelia stanol study was conducted to verify these findings in a 12 month large-scale randomised double-blind study (Miettinen T. A,. Puska P,. Gylling H,. Vanhanen H. and Vartiainen E. (1995). *N. Engl. J. Med.* 333, 1308-1312). The results from this study show that a daily intake of 1.8-2.6 g of fat-soluble sito-stanol ester (calculated as free stanol) administered in a margarine decreased the total cholesterol with 10% and the LDL-cholesterol with 14% compared to the reference group having a margarine without added fat-soluble stanol ester.

Stanol fatty acid esters with fatty acids based on commercially available high PUFA vegetable oils such as sunflower oil, corn oil, soybean oil, safflower oil, cottonseed oil or their blends will show too high texturizing properties in vegetable oils or their blends in order to be incorporated into foods like salad oils, cooking oils, easily pourable salad dressings, sauces and mayonnaises in amounts high enough for an adequate daily intake of stanols and sterols in order to obtain an optimal cholesterol lowering effect. This problem will be solved by the present invention.

Another problem in the prior art is the production of food products with very high contents of phytosterols in a form that could be added to a variety of food products in concentration high enough to supply by normal food intake the daily adequate amount of sterols and/or stanol for optimum effect on blood cholesterol levels. This was partly solved in the prior art by producing the fatty acid esters of the phytosterols and phytostanols. However, by using the sterol and/or stanol fatty acid esters according to the present invention even higher amounts of phytosterols and phytostanols can successfully be used in certain vegetable oil based food products like salads oils, cooking oils, easily pourable salad dressings, sauces and mayonnaises.

Furthermore, sterol and/or stanol esters according to the current invention can successfully be used in spread type of products such as margarines, low-fat spreads, spreadable cheeses, butter etc., wherever there is a desire to use conventional triglyceride hardstock and not utilise the texturizing properties obtainable from sterol esters and/or stanol esters in the manufacturing of such products. One reason for such desire can be that utilising of sterol and/or stanol esters according to the present invention is technically not so demanding, making it more easy and feasible to produce such products with conventional production technology.

Capsules with free sterols and stanols suspended in safflower oil or mono-olein have been used as a mean for lowering elevated cholesterol levels. E.g. Denke (Denke (1995) Am. J. Clin. Nutr. 61, 392-396) fed 4 capsules/meal of free stanol suspended in safflower oil to men with moderate hypercholesterolemia as part of a cholesterol-lowering diet. The total daily intake of sitostanol was 3000 mg provided in 12 capsules. The sitostanol capsule regimen did not significantly reduce LDL cholesterol levels compared to the diet alone.

Due to the low solubility of free sitostanol in vegetable oils the use of capsules containing free sitostanol suspended in safflower oil does not ensure that the si-tostanol is efficiently distributed into the fat phase of the food digest. This problem can be overcomed by using capsules based on sterol and/or stanol esters according to the present invention, since these esters are liquid at body temperature and will easily be dissolved into the fat phase of the food digest. In addition no triglyceride fat or mono-olein is needed as a dispersing agent, making it possible to reduce the size or amount of capsules needed to supply the daily needed optimal amount of sterols and/or stanols.

SUMMARY OF THE INVENTION

The present invention is based on the finding that sterol and/or stanol fatty acid ester compositions, in which more than 50% of the fatty acid moieties comprises polyunsaturated fatty acids (PUFA), preferentially more than 60% and more preferred more than 65%, and less than 7% comprises saturated fatty acids (SAFA), preferentially less than 5%, show basically no texturizing properties and can thus be used in food products were such a texturizing effect is due to product quality or production technology reason undesirable or is wanted only to a very limited degree.

The invention is further based on the fact that stanol fatty acid esters based on rapeseed oil with a low content of saturated fatty acids and a high content of unsaturated fatty acids (mainly monounsaturated) give a DSC melting curve (FIG. 1), where all stanol fatty acid esters have co-crystallized. Thus, this blend of stanol fatty acid esters melts in one distinct melting peak measured with differential scanning calorimetry (DSC) after a directed crystallisation procedure. The DSC melting curve is obtained after melting the sample (about 8 mg) at 75° C. for 10 minutes, after which the sample is crysallised by cooling at 10° C./minute to −50° C., where it is kept for five minutes. The melting curve is obtained by heating at 10° C./minute to 70° C.

BRIEF DESCRIPTION OF THE DRAWINGS

FIG. 3 shows DSC melting curves for stanol esters based on soybean fatty acids; the stanol esters fractionated to a fatty acid composition of 64.8% PUFA and 7.5% SAFA is compared to the DSC curve in FIG. 2.

FIG. 4 shows DSC melting curves for stanol esters based on soybean fatty acids, the stanol esters fractionated to a fatty acid composition of 69% PUFA and 5.8% SAFA is compared to the DSC curve in FIG. 2.

DETAILED DESCRIPTION OF THE INVENTION

Figure 1:
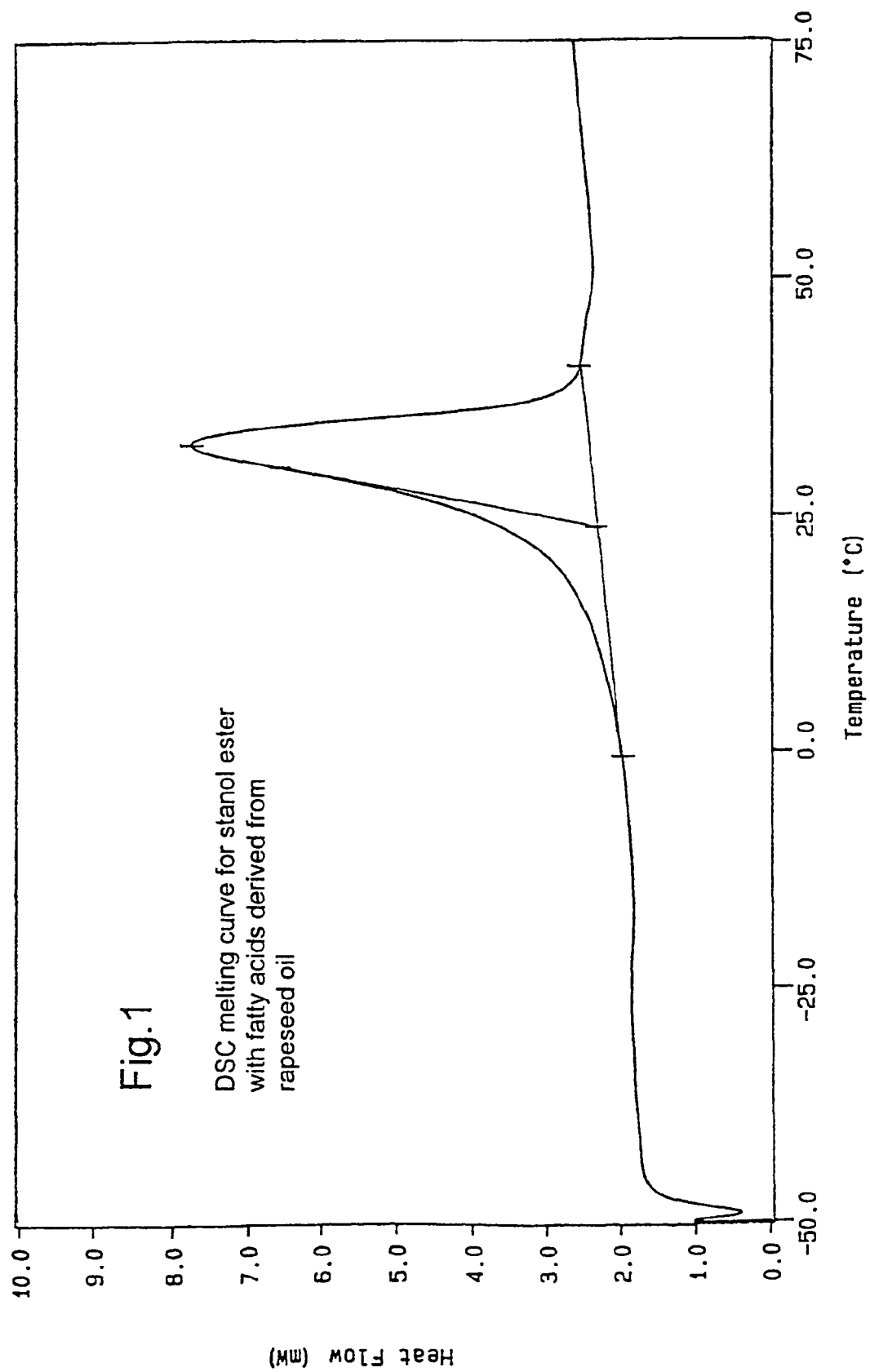
FIG. 1 shows the DSC melting curve for stanol esters based on rapeseed fatty acids.

Surprisingly it was found that stanol fatty acid esters based on vegetable high PUFA oils show a very different melting DSC curve (FIG. 2, stanol esters based on soybean fatty acids), where the stanol esters of polyunsaturated fatty acids seem to be melting (melting range from about −5° C. to about 25° C.) in a distinct temperature range, different from the monounsaturated and saturated stanol fatty acid esters.

Based on the behavior of the low erucic rapeseed oil based stanol fatty acid ester blend, showing only one uniform melting peak as measured by DSC, a similar PUFA stanol ester directed crystallising and melting behavior could be obtained, if the fatty acid composition of the stanol fatty acid esters is changed to markedly lower the content of saturated fatty acids and to somewhat increase the content of polyunsaturated fatty acids compared to natural high PUFA liquid vegetable oils.

High PUFA sterol and/or stanol esters can be produced by e.g. the method described in U.S. Pat. No. 5,502,045 (Miettinen et al.) by direct esterification of fatty acid alcohol esters obtained from high PUFA vegetable oils or their blends. Alternatively direct, preferably catalytic esterification methods or enzymatic esterification methods such as out-lined in EP-195 311 (Myojo et al.) can be used.

Sterol and/or stanol ester blends according to this invention can also be obtained by the method described in U.S. Pat. No. 5,502,045 by direct esterification of a fatty acid alcohol ester having appropriate fatty acid composition.

Furthermore, the fact that the PUFA fraction of stanol esters in high PUFA vegetable oil based stanol esters melts in a distinct temperature range indicates that stanol esters based on high PUFA vegetable oils can be subjected to fractionation in order to obtain stanol esters with decreased contents of saturated fatty acids and increased contents of polyunsaturated fatty acids in the fatty acid part.

It is obvious to persons skilled in the art that all fractionation processes of prior art including dry, wet, detergent and solvent fractionation processes or combinations of these can be used to obtain the desired compositions. Due to the high viscosity of stanol esters dry fractionation is not an optimal approach for achieving desired results. E.g. stanol fatty acid esters based on low erucic acid rapeseed oil show following viscosity values at specific temperatures: 728 cP at 48° C., 80 cP at 100° C. Corresponding values for low erucic acid rapeseed are 48.3 cP at 49.3° C. and 8.4 cP at 100° C. The problem with the high viscosity can however be overcomed by carrying out the fractionation step in a blend of sterol ester and/or stanol ester and a vegetable oil or a blend of vegetable oils. Preferably the used vegetable oil or vegetable oil blend is the one desired in the final food product. The vegetable oil markedly decreases the viscosity of the sterol and/or stanol ester vegetable oil blend, making the fractionation feasible with any commercially available dry fractionation process of prior art.

Another possibility is to utilise the excess of high PUFA alcohol esters present in the oily phase obtained after the esterification of high PUFA sterol and/or stanol ester according to the method described in the U.S. Pat. No. 5,502,045 (Miettinen et al.). This high PUFA alcohol ester sterol and/or stanol ester mixture can as such be subjected to a fractionation step to remove higher melting sterol and/or stanol esters.

Saturation of a plant sterol blend to corresponding plant stanol blend causes marked differences in melting properties of corresponding sterol/stanol esters with the same fatty acid composition. E.g. vegetable oil based sterol ester with low erucic acid rapeseed oil fatty acids and corresponding stanol fatty acid ester showed the following amounts of solid fat contents (percent of total fat) at different temperatures as measured by NMR-technique:

|  | 10° C. | 20° C. | 30° C. | 35° C. | 40° C. |
| --- | --- | --- | --- | --- | --- |
| sterol | 40.5 | 11.6 | 3.5 | 1.7 | 1.1 |
| stanol | 82.3 | 70.2 | 34.9 | 9.4 | 5.2 |

Based on these data, it is obvious to persons skilled in the art that any blend of sterol and/or stanol fatty acid esters will show solid fat content values in the intermediate range of the sterol and stanol fatty acid esters with corresponding fatty acid compositions.

The present invention further makes it possible to incorporate increased amounts of plant sterols, plant stanols or their blends into specific foods, such as salad and cooking oil, easily pourable salad dressings, sauces and mayonnaises, where the content of sterol and/or stanol ester based on ordinary high PUFA fatty acid compositions would have to be reduced in order not to change the physical and sensoric properties of the final product. It is evident from the data presented, that the present invention makes it easier to supply a daily adequate amount for optimal cholesterol reducing efficacy from such specific products, without having to compromise on the quality of the product.

Another area of potential use for sterol esters, stanol esters or their blends with a high PUFA and low SAFA fatty acid composition is capsules with totally liquid sterol and/or stanols esters at body temperature, rapidly dissolving into the fat phase of the food digest in the stomach. The use of sterol and/or stanol esters according to the present invention will overcome prior problems with capsules based on free sterols and/or stanols suspended in vegetable oils or mono-olein.

It is believed that the optimum cholesterol lowering effect is achieved, if the sterols, stanols or their blends are efficiently dissolved into the fat phase of the digesting food. It is assumed that the sterols and stanols need to be dissolved in the fat phase of the digesting food in order to have an efficient reducing effect on the cholesterol absorption. Furthermore, dietary cholesterol accounts for only about ⅓ of the total cholesterol amount entering the digestive tract daily. Biliary cholesterol is the main source of intestinal cholesterol.

In order to have an optimal cholesterol reducing effect from the use of plant sterols and stanols, they should be present in the digestive tract whenever food intake causes the gallbladder to contract. Therefore, the use of fat-soluble sterol and stanol esters incorporated into regular food products seems to be an optimal choice of delivering the sterols and/or stanols.

However, there are many occasions, when plant sterol and/or stanol enriched food products are not available. Therefore, the use of capsules, e.g. gelatine capsules, or tablets would be another possible approach for delivering the optimal daily dose at meals, making the sterol/stanol regimen available all the time. A sterol or stanol fatty acid esters capsule with a fatty acid composition according to the present invention would be totally melted at body temperature and dissolve fast in the fat-phase of the food digest. The efficient dissolving of sterol and/or stanol esters according to the present invention will be ensured without the use of additional dissolving lipid materials, since the sterol and/or stanol esters according to the present invention will be liquid at body temperature. In addition no triglyceride fat or mono-olein is needed as a dispersing agent, making it possible to reduce the size or amount of capsules needed to supply the daily needed optimal amount of sterols and/or stanols.

Clear cooking and salad oils with much higher plant sterol contents (sterol equivalent) than disclosed in the prior art can preferably be produced by using sterol esters according to the present invention. The clear cooking and salad oils disclosed in the prior art are based on the use of phytosterol esters based on individual saturated fatty acid moieties with less than 12 carbon atoms or individual unsaturated fatty acids with up to 24 carbon atoms. The limited amount of saturated fatty acids contained in the sterol and/or stanol esters according to the present invention is primarily based on the saturated fatty acids naturally contained in the parent high PUFA vegetable oil or vegetable oil blend, namely saturated fatty acids with more than 14 carbon atoms. The sterol and/or stanol fatty acid esters according to the present invention can be utilised in low-fat products and in products for consumers wishing to eat only small amounts of fat-containing foods. The stanol esters according to the invention can also be used in a somewhat increased amount compared to prior art. Therefore, by using sterol and/or stanol fatty acid esters according to the present invention the daily dosage needed for effective lowering of the cholesterol level can easily be accomplished.

The compositions according to the invention also have the obvious positive effect from a nutritional point of view as the fatty acid composition in the food product is changed to a lower content of saturated fatty acids and a higher content of unsaturated fatty acids. Based on the fact that the sterol and/or stanol part is unabsorbable also the amount of absorbable fat is reduced in the food products, since the sterol and/or stanol esters are replacing about an equal amount normal triglyceride fat.

The use of stanol fatty acid esters, wherein the fatty acid moiety comprises a blend of less than 7% of saturated fatty acids and more than 50% of polyunsaturated fatty acids, more preferably wherein less than 5% of the fatty acid moieties comprises saturated fatty acids, is the preferred way of practicing the present invention. The most preferably practice of the present invention uses stanols that comprise sitostanol and optionally campestanol.

The term high PUFA vegetable oils is in this specification meant to be vegetable oils or vegetable oil blends containing more than 50% polyunsaturated fatty acids and at least 7% saturated fatty acids of the fatty acid composition. Typical high PUFA oils include sunflower oil, corn oil, soybean oil, safflower oil, cottonseed oil or their blends. The amount of saturated fatty acids in the fatty acid composition is about 7.5-49%, more typically about 8-25% and most typically about 10-20%.

By the term phytosterol is in this specification meant 4-desmethyl sterols, 4-monomethyl sterols, and 4,4-dimethyl sterols (triterpene alcohols) or their blends. By the term phytostanol is in this specification meant 4-desmetyl stanols, 4-monomethyl stanols and 4,4-dimethyl stanols preferably obtained by hydrogenation of the corresponding phytosterol. Typical 4-desmethyl sterols are sitosterol, campesterol, stigmasterol, brassicasterol, 22-dehydrobrassicasterol, Δ5-avenasterol. Typical 4,4-dimethyl sterols are cycloartenol, 24-metylenecycloartanol and cyclobranol. Typical phytostanols are sitostanol, campestanol and their 24-epimers, cycloartanol and saturated forms obtained by saturation of triterpene alcohols (cycloartenol, 24-metylenecycloartanol and cyclobranol). By the terms phytosterols and phytostanol is in this specification further meant all possible natural blends of 4-desmethyl sterol and stanols, 4-monomethyl sterols and stanols, 4,4-dimethyl sterols and stanols and mixtures of natural blends. By the terms phytosterols and phytostanols is in this specification further meant any individual 4-desmethyl sterol, 4-monomethyl sterol or 4,4-dimethyl sterol or their corresponding saturated forms.

The terms plant sterol and plant stanol are used in this specification as synonyms to phytosterol respectively phytostanol. Sterol and stanol shall also mean phytosterol respectively phytostanol.

Polyunsaturated fatty acids are here defined as fatty acids containing 2 or more double bonds. Preferentially the double bonds should have cis configuration, but one or more double bonds could be in trans configuration. It is known that many commercially available vegetable oils due to termal isomerisation in the deodorisation process contain % levels of polyunsaturated fatty acids containing one or more double bond with trans configuration. In addition the double bonds can be either so-called methylene interrupted or conjugated. Typical vegetable oil derived polyunsaturated fatty acids are linoleic, linolenic and γ-linolenic acid, but also polyunsaturated fatty acids from fish oils such as eicosapentaenoic and docosahexaenoic acid can be utilised.

By the term saturated fatty acids is meant fatty acids with 4-24 carbon atoms not having any double bonds, thereby including both straight chain and branched fatty acids.

By the term high PUFA sterol and/or stanol esters is meant sterol and/or stanol esters produced preferentially with fatty acids from high PUFA vegetable oils, but also fish oil derived polyunsaturated fatty acids or blends of vegetable and fish oil derived polyunsaturated fatty acids can be used.

The sterol esters, stanol esters or their blends can preferably be produced by the method outlined in U.S. Pat. No. 5,502,045 (Miettinen et al.) using a fatty acid alcohol ester with a specified fatty acid composition according to the present invention. The fatty acid alcohol esters can be produced by any process known in the art, such as solvent or detergent fractionation of alcohol fatty acid esters obtained from a high PUFA liquid vegetable oil or blends of high PUFA oils. Corresponding blends of fatty acid alcohol esters can also be obtained by distillation procedures under reduced pressure. Such distillation procedures can preferentially be used to remove saturated fatty acids with 16 or less carbon atoms. Fatty acid alcohol esters with the defined fatty acid compositions can also be obtained by alcoholysis of vegetable oils or oil blends with reduced contents of saturated fatty acids, obtained e.o. according to the U.S. Pat. No. 5,670,348 (William et al.).

The sterol and/or stanol esters can also be produced by direct, preferably catalytic esterification methods between free fatty acids or fatty acid blends of said composition and the sterol and/or stanol, In addition sterol and/or stanol esters can also be produced by enzymatic esterification e.g. as out-lined in EP-195 311.

In addition blends of polyunsaturated fatty acids can be used for obtaining sterol and/or stanol esters with the defined composition.

Stanol esters and/or sterol esters with the defined fatty acid compositions can further be obtained by commercially applied fractionation processes, such as dry, detergent and wet-type fractionation of stanol and/or sterol fatty acid esters obtained by esterification of high PUFA fatty acids derived from e.g. vegetable oil or oil blends by methods based on e.g. the transesterification process outlined in U.S. Pat. No. 5,502,045, any direct preferably catalytic esterification process or by the use of an enzymatic esterification process e.g. as outlined in EP 195 311. Especially fractionation from solvents can be used for preparing desired sterol and/or stanol ester compositions. When using enzymatic esterification processes such as out-lined in EP 195 311 the fractionation can preferably be carried out directly in the reaction solvent used in the esterification process after removing the enzyme and possible water phase.

In a preferred embodiment vegetable oils containing desired sterol and/or stanol fatty acid esters can be obtained by dissolving 15-50 weight-% (preferentially 15-25%) of sterol and/or stanol fatty acid esters obtained by an esterification process such as that disclosed in U.S. Pat. No. 5,502,045 by using a high PUFA vegetable oil or a mixture of high PUFA vegetable oils as a source for the fatty acids. The so obtained sterol and/or stanol esters vegetable oil blend is heated and mixed to totally dissolve the sterol and/or stanol esters after which conventional winterising or any fractionation process of prior art is carried out. E.g. a winterising/batch dry fractionation process can be carried out at 5-20° C. depending on the type of sterol ester and/or stanol ester used. Then the solid part of the sterol or stanol ester is removed e.g. by vacuum filtering and the liquid part containing the sterol ester, stanol ester or their blend with the desired fatty acid composition according to the invention is subjected to normal deodorising before use in the manufacturing of the end product or bottled to be used as cooking or salad oil. It is obvious to those skilled in the art that any type of fractionation process in addition to the winterising or batch dry fractionation processes can be utilised for crystallising and removing sterol and/or stanol fatty acid esters with higher melting points, i.e. sterol and/or stanol fatty acid esters based on saturated fatty acids namely.

In an other preferred embodiment stanol esters and/or sterol esters with the defined fatty acid compositions can further be obtained by utilising the excess of fatty acid methyl ester of the high PUFA sterol and/or stanol ester blend obtained after the direct esterification disclosed in U.S. Pat. No. 5,502,045 (Miettinen et al.). After the drying step the sterol and/or stanol ester fatty acid alcohol ester mixture is cooled to 10-25° C., depending on the composition of the sterol and/or stanol ester produced, and the higher melting components are allowed to crystallise for 4-6 hours. Optionally additional fatty acid alcohol ester is added to facilitate the fractionation process. Any fatty acid alcohol ester may be used, but the use of high PUFA alcohol ester is preferred. After filtration the clear oily phase is preferably deodorised to remove the excess fatty acid alcohol esters and to obtain a tasteless sterol and/or stanol ester.

The sterol and/or stanol esters obtained as such can preferably be mixed into oil blends prior to the final deodorising step of the fat blend to be used in the production of the final food product. Alternatively the sterol and/or stanol ester can be deodorised as such and used as such e.g. in the production of capsules. Furthermore the deodorised sterol and/or stanol esters according to the present invention can be dissolved in the vegetable oil or vegetable oil blend to be used as such as e.g. salad or cooking oil or to be used in the production of specific food, especially low-fat food products, salad dressings, mayonnaises, sauces or any fat-containing food product, where a sterol and/or stanol ester with no or limited texturing properties for product quality or production technology reasons are desirable. In another embodiment the oil can be added to the mixture already before the fractionation to facilitate the procedure.

Vegetable oils containing desired sterol esters, stanol esters or their blends can further be produced by carrying out the esterification in the oil blend in a similar way as described in GB patent 1 405 346 (Baltes et al.). The obtained totally interesterified oil is subjected to a subsequent fractionation step such as a winterising step to obtain a vegetable oil containing desired amounts of sterol esters, stanol esters or their blends. Alternatively, an esterified vegetable oil sterol and/or stanol ester stock blend with a high content of sterol and/or stanol ester (20-90 weight-% sterol and/or stanol ester) can be produced by the same approach. The obtained triglyceride sterol and/or stanol ester blend can then be blended in proportions needed to obtain the desired content of sterol esters, stanol esters or their blends with the unesterified vegetable oil or vegetable oil blend to be used in the final product before the winterisation or fractionation process to remove mainly higher melting sterol and/or stanol esters with saturated fatty acids. Furthermore, the fractionation process can be carried out after the esterification step, utilising the excess of fatty acid alcohol esters. Optionally additional fatty acid alcohol ester is added to facilitate the fractionation process.

In addition sterol and/or stanol ester compositions according to the invention can be produced utilising "fatty acid starting materials" such as fatty acids, fatty acids alcohol esters or oils obtained by processes including e.g. utilising of microorganisms enzymes or new breedings of oil producing plants.

The following Figures illustrates the invention:

FIG. 1: A DSC melting curve for stanol esters based on rapeseed fatty acids.

Figure 2:
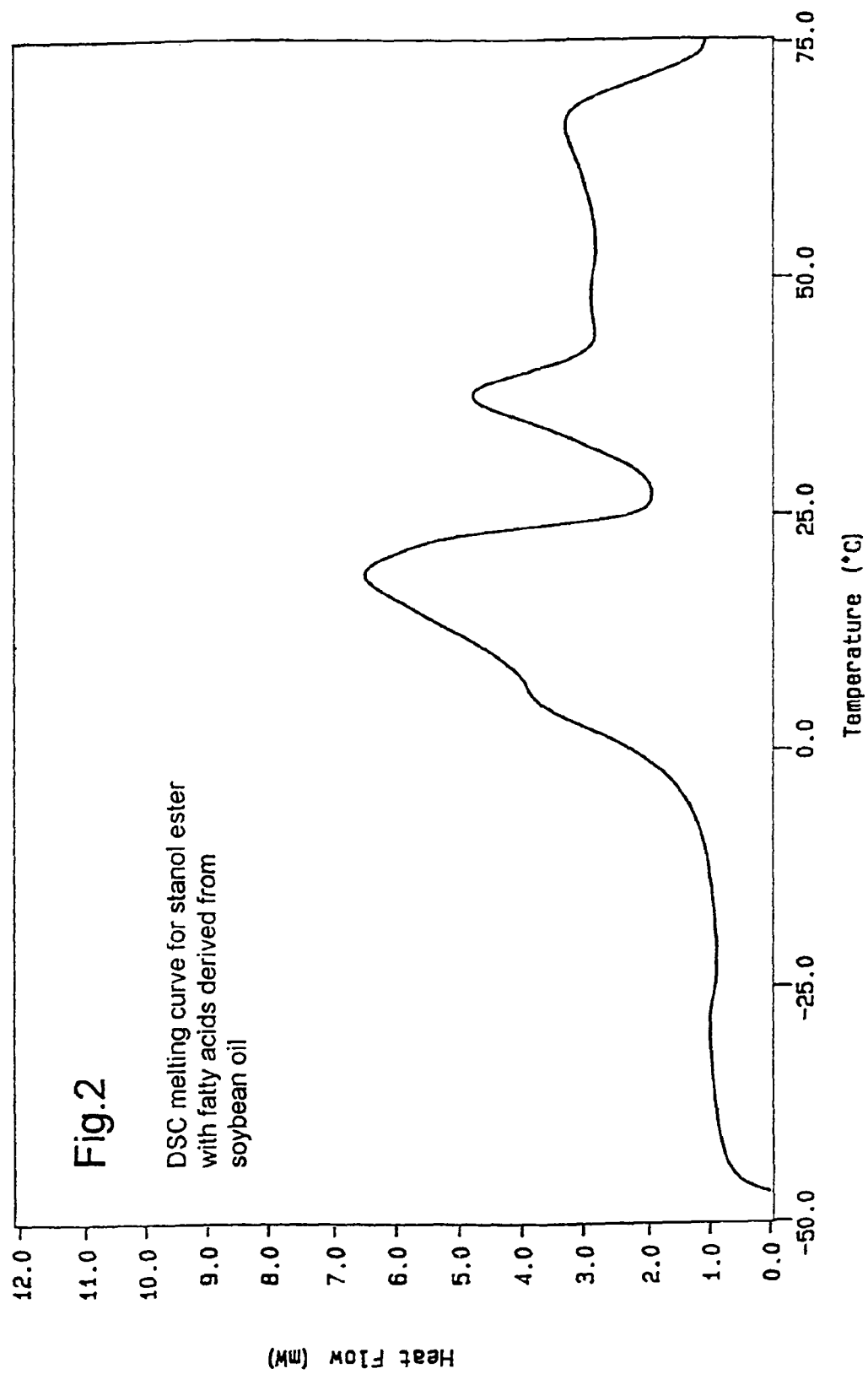
FIG. 2 shows the DSC melting curve for stanol esters based on soybean fatty acids.

FIG. 2: A DSC melting curve for stanol esters based on soybean fatty acids.

FIG. 3: DSC melting curves for stanol esters based on soybean fatty acids; the stanol esters fractionated to a fatty acid composition of 64.8% PUFA and 7.5% SAFA is compared to the DSC curve in FIG. 2.

FIG. 4: DSC melting curves for stanol esters based on soybean fatty acids; the stanol esters fractionated to a fatty acid composition of 69% PUFA and 5.8% SAFA is compared to the DSC curve in FIG. 2.

The following examples are presented in order to disclose the present invention in more detail.

EXAMPLE 1

Preparation of Stanol Fatty Acid Esters Based on Soybean Oil Fatty Acids

The stanol fatty acid esters were produced in a pilot scale. 6 kg plant stanol (composition: 90% sitostanol, 8% campestanol, 1.5% sitosterol+trace amounts of other unsaturated sterols, obtained by hydrogenation of a commercial tall oil sterol blend (Kaukaus Oy)) was dried for 6 hours at 60° C. in vacuo to remove moisture. The dried stanol was blended with 8,6 kg soybean oil methyl ester mixture and dried at 110-120° C. The temperature of the dry mixture was reduced to 90-95° C. and the sodium ethylate catalyst (21 g) was added. The temperature was increased to 110° C. and the reaction was carried out under vacuum (10-20 mmHg). The conversion was monitored by fast HPLC analysis. Once >98% conversion was achieved, the temperature was reduced to 100° C. and 30 weight-% water or acidified water was added to destroy the catalyst. The water phase was removed and the oily phase was rewashed with water. The oily phase was dried at 110° C. and the dry material was bleached using 1 weight-% bleaching aid (Tonsil Optimum FF, Südchemie, Germany) for 20 minutes at 110° C. After removal of the bleaching aid by filtration a standard pilot scale deodorisation (batch deodoriser, capacity 9 kg) was carried out to remove the excess of soybean oil methyl esters and to obtain a tasteless stanol ester product.

EXAMPLE 2

Preparation of Tall Oil Based Sterol Fatty Acid Ester Based on Soybean Fatty Acids Sterol ester fatty acid esters based on soybean oil derived fatty acids were prepared by the same procedure as outlined in Example 1, except that the stanol was exchanged for an equivalent amount of commercial tall oil sterol blend (Kaukas Oy).

EXAMPLE 3

Preparation of Vegetable Oil Based Sterol Fatty Acid Ester with Fatty Acids Derived from Sunflower Oil A sterol fatty acid ester blend with fatty acids derived from sunflower oil was prepared in laboratory scale. 295 g vegetable oil based sterols (ADM: composition: 48.3% sitosterol, 26.4% campesterol 15.2% stiomasterol 2.4% brassicasterol, 2.7% sitostanol, 0.9% campestanol and 4.1% others) was dissolved by heating and use of vacuum in 424 g sunflower methyl esters in a 1l glass reactor equipped with a mechanical stirrer. The blend was dried at 130° C. and a vacuum of <5 mmHg. The temperature of the dried mixture was reduced to 97° C. and 3.6 g sodium ethylate was added. The reaction was carried out at 130° C. under a final vacuum of <5 mmHg. After 4 hours the temperature was reduced to 99° C. and the oily mixture was washed twice with 30 weight-% water. The oily phase was removed and dried at 112° C. under vacuum (<5 mmHg), after which the oily phase was bleached using 2 weight-% bleaching aid (Trisyl Silica) for 40 minutes at 110° C. under vacuum (<5 mmHg). After removing the bleaching aid by filtering (6 μm) sterol esters with fatty acids derived from sunflower oil were obtained by distilling off the excess fatty acid methyl esters by heating on an oil bath at 190-195° C. with the methyl esters boiling at 130-140° C. at a vacuum of <0.1 mmHg.

EXAMPLE 4

Preparation of a Stanol Fatty Acid Esters with a Decreased Content of Saturated Fatty Acids and an Increased Content of Polyunsaturated Fatty Acids with Solvent Fractionation 10 g of the stanol ester obtained by the procedure outlined in Example 1 was dissolved in 90 ml n-hexane in a 200 ml centrifuge tube. The mixture was kept at 10° C. for 19 hours, after which the mixture was centrifuged in a temperature programmable centrifuge. The hexane phase was removed and the hexane was evaporated. The obtained stanol ester contained 64.8% polyunsaturated fatty acids (compared to 58.4 in the starting stanol ester blend) and 7.5% saturated fatty acids (compared to 16.7 in the starting stanol ester). The obtained DSC melting curves after a directed crystallisation are shown in FIG. 3.

In an other experiment the 10% stanol ester hexane mixture was crystallised at 5° C. for 19 hours. After evaporation of the hexane, the stanol ester obtained from the hexane phase contained 69% polyunsaturated fatty acids and 5.8% saturated fatty acids. The DSC melting curve obtained after a directed crystallisation process is shown in FIG. 4 as well as the curve for the starting stanol ester.

EXAMPLE 5

Fractionation of Soybean Stanol Esters from Blends of Stanol Esters and Vegetable Oil(s)

Since the viscosity of stanol esters is high and limits the use of direct crystallisation processes a method was developed whereby the viscosity could be reduced. This method is based on dissolving the stanol ester in a vegetable oil or vegetable oil blend prior to carrying out the fractionation step. The vegetable oil or vegetable oil blend is chosen based on the desired oil in the final food product.

25 weight-% stanol fatty acid ester produced according to the procedure outlined in Example 1 was dissolved in 75 weight-% sunflower oil. The mixture was heated to about 70° C. to dissolve the stanol fatty acid esters. The mixture was then cooled and kept at 9° C. for 5 hours. The obtained solid phase was filtered off and a clear sunflower oil with a stanol equivalent content of 12.6 weight-% corresponding to about 21 weight-% of stanol ester was obtained. The sunflower oil stanol ester blend remained clear at 6° C. for 48 hours. The stanol fatty acid ester in the obtained sunflower oil was analysed for its fatty acid composition and was found to contain 67.9% of polyunsaturated fatty acids and 3.5% saturated fatty acids. It is obvious that any commercial dry fractionation process can be used to carry out the fractionation to obtain sterol and/or stanol ester compositions defined by this invention. The dry fractionation is made much more convenient by reducing the viscosity by blending the sterol and/or stanol ester with a vegetable oil or vegetable oil blend. For different processes and different sterol and/or stanol ester specific processing conditions can be found in order to obtain desired sterol and/or stanol compositions.

EXAMPLE 6

Preparation of Stanol Fatty Acid Esters with a Decreased Content of Saturated Fatty Acids and an Increased Content of Polyunsaturated Fatty Acids by Carrying out a Fractionation Process Directly After the Esterification Step, Utilising the Excess of High PUFA Oil Fatty Acid Alcohol Ester.

Soybean oil based stanol fatty acid esters were produced according to Example 1, except that the obtained stanol ester soybean oil fatty acid methyl ester blend was subjected to a fractionation process directly after the drying step. The temperature was decreased to 20° C. for 5 hours and the hard fraction was filtered off by the use of vacuum filtration. The excess soybean fatty acid methyl esters were removed during the final deodorisation process to obtain a tasteless stanol ester.

EXAMPLE 7

Preparation of Stanol Fatty Acids with Vegetable Oil as Solubilising Media with a Subsequent Fractionation Process.

The stanol fatty acid esters were produced in a pilot scale. 3 kg plant stanol (composition: 90% sitostanol, 8% campestanol 1.5% sitosterol obtained by hydrogenation of a commercial tall oil sterol blend (Kaukas Oy)) was dried for 6 hours at 60° C. in vacuo to remove moisture. The dried stanol was blended with 3 kg of soybean oil and 4.3 kg soybean oil methyl ester mixture and dried at 110-120° C. The temperature of the dry mixture was reduced to 90-95° C. and the sodium ethylate catalyst (21 g) was added. The temperature was increased to 110° C. and the reaction was carried out under vacuum. The conversion was monitored by fast HPLC analysis. Once >98% conversion of free stanols to stanol esters was achieved, the temperature was reduced to 100° C. and 30 weight-% water or acidified water was added to destroy the catalyst. The water phase is removed and the oily phase was rewashed with water. The oily phase was dried at 110° C. and the dry material was bleached using 1 weight-% bleaching aid (Tonsil Optimum FF, Südchemie, Germany) for 20 minutes at 110° C. After removal of the bleaching aid by filtration, the excess of soybean oil fatty acid methyl esters were removed and the intersterified oil stanol ester blend was lightly deodorised in a standard pilot scale deodorisation (batch deodoriser, capacity 9 kg). 40 weight-% of the obtained mixture was then blended with 60 weight-% sunflower oil and a fractionation step according to Example 4 was carried out. The obtained liquid fraction was deodorised to obtain a vegetable oil stanol ester blend with a stanol equivalent of 12.2 weight-%.

EXAMPLE 8

Direct Preparation of Stanol Fatty Acid Esters with a Decreased Content of Saturated Fatty Acids and an Increased Content of Polyunsaturated Fatty Acids.

Soybean oil fatty acid methyl esters were subjected to fractional distillation at 182° C. and 10 mmHg to mainly reduce the amount of palmitic acid content. The obtained fatty acid methyl ester contained 67.2% polyunsaturated fatty acids and 4.8% saturated fatty acids. Stanol fatty acids were produced in laboratory scale using 300 g hydrogenated vegetable oil stanols (composition: sitostanol 67.3%, campestanol (+24-methyl cholestanol) 30.3%, sitosterol 1.5%, carnpesterol 0.8% and others 0.4%), and 322 g distilled soybean fatty acid methyl esters. The reaction was carried out in a 1.5 liter glass reactor equipped with a mechanical stirring device. The conditions used were the same as outlined in Example 1. Since no laboratory scale deodorising equipment was available the obtained stanol esters were not fully purified. However, the fatty acid composition of the stanol ester was equal to the fatty acid composition of the soybean fatty acid methyl ester used in the esterification reaction.

It is obvious to persons skilled in the art that sterol and/or stanol esters with fatty acid compositions specified in this invention also can be obtained by esterification with fatty acid alcohol esters with the specified fatty acid composition produced by any method of prior art. Furthermore, it is obvious that sterol and/or stanol esters according to the invention can be obtained via any esterification process, such as direct, preferentially catalytic esterification, transesterification or enzyme facilitated esterification. It is also obvious that any blend of sterol and stanol can be utilised in the preparation of sterol and/or stanol fatty acid compositions according to the present invention.

Examples 4 to 7 clearly show that high PUFA sterol and/or stanol esters can be processed to remove higher melting sterol esters and stanol esters to obtain sterol and/or stanol compositions according to the present invention. High PUFA sterol and/or stanol esters can be produced based on fatty acids from any high PUFA vegetable oil such as soybean oil, sunflower oil, corn oil, safflower oil, cottonseed oil or their blends. It is obvious to persons skilled in the art that oils or fat blends with not so elevated contents of polyunsaturated fatty acids (<50%) can also be used as starting material for the fatty acid part to be contained in the sterol and/or stanol ester composition according to the invention.

It is obvious to persons skilled in the art that any sterol or stanol composition or blends of commercially available sterols or their corresponding stanols can be used as starting material for obtaining sterol and/or stanol ester blends according to the present invention. Furthermore, it is obvious to persons skilled in the art that any natural blend of plant sterols containing 4-desmetyl sterols, 4-monomethyl sterols and 4,4-dimethyl sterols (triterpene alcohols) or their corresponding saturated sterols (stanols) or blends of sterols and stanols can be used as a starting material for the preparation of sterol and stanol esters according to this invention. Such possible sources of plant sterol and triterpene alcohols are rice bran oil or oryzanol obtained from rice bran oil, sterols obtained from shea butter, or linseed oil.

What is claimed is:

1. A method for preparing an edible oil or fat blend with elevated sterol and/or stanol content comprising liquid vegetable oil and a sterol and/or stanol fatty acid ester composition, wherein less than 7% of the fatty acid moieties comprises saturated fatty acids and more than 50% comprises polyunsaturated fatty acids, comprising fractionating a mixture of a high PUFA sterol and/or stanol ester and a vegetable oil or oil blend to remove higher melting sterol and/or stanol esters, to prepare a composition wherein less than 7% of the fatty acid moieties comprises saturated fatty acids and more than 50% comprises polyunsaturated fatty acids.

2. The method according to claim 1, wherein the polyunsaturated fatty acids are derived from high polyunsaturated vegetable oils or high polyunsaturated vegetable oil blends.

3. The method according to claim 2, wherein the high polyunsaturated vegetable oils are selected from the group consisting of: sunflower oil, corn oil, soybean oil, safflower oil, and cottonseed oil.

4. The method according to claim 1, wherein the polyunsaturated fatty acids are derived from fish oil or a blend of vegetable oil or oils and fish oil.

5. The method according to claim 1, wherein the high PUFA sterol and/or stanol ester are produced by esterifying a high polyunsaturated fatty acid mixture with free sterol and/or stanol by direct esterification or enzymatic esterification or esterifying an alcohol ester of fatty acid mixture of said composition with free sterol and/or stanol in the presence of an interesterification catalyst.

6. The method according to claim 5, wherein the direct esterification is catalytic esterification.

* * * * *